(12) United States Patent
Williams et al.

(10) Patent No.: US 7,250,129 B2
(45) Date of Patent: Jul. 31, 2007

(54) SOFT, FLEXIBLE COMPOSITION AND METHOD FOR MAKING SAME

(75) Inventors: Karla E Williams, Westwood, NJ (US); Paul D Zwick, Cuyahoga Falls, OH (US)

(73) Assignee: Playtex Products, Inc., Westport, CT (US)

( * ) Notice: Subject to any disclaimer, the term of this patent is extended or adjusted under 35 U.S.C. 154(b) by 565 days.

(21) Appl. No.: 10/836,309

(22) Filed: Apr. 30, 2004

(65) Prior Publication Data

US 2005/0070645 A1    Mar. 31, 2005

Related U.S. Application Data

(60) Continuation-in-part of application No. 09/648,883, filed on Aug. 25, 2000, now Pat. No. 6,756,434, which is a division of application No. 09/075,097, filed on May 8, 1998, now Pat. No. 6,254,565, which is a continuation of application No. 08/547,766, filed on Oct. 24, 1995, now Pat. No. 5,986,000, which is a continuation-in-part of application No. 08/447,289, filed on May 22, 1995, now Pat. No. 5,681,894.

(51) Int. Cl.
B29C 45/46 (2006.01)
C08L 53/02 (2006.01)

(52) U.S. Cl. ................... 264/328.17; 264/330
(58) Field of Classification Search ........... 264/328.17, 264/330
See application file for complete search history.

(56) References Cited

U.S. PATENT DOCUMENTS

| | | | | |
|---|---|---|---|---|
| 4,197,377 A | * | 4/1980 | Bohm et al. ................... | 525/99 |
| 4,386,188 A | * | 5/1983 | Grancio et al. ................ | 525/96 |
| 4,593,063 A | * | 6/1986 | Jones et al. .................. | 524/505 |
| 4,880,878 A | * | 11/1989 | Himes et al. .................. | 525/89 |
| 5,191,024 A | * | 3/1993 | Shibata et al. ............... | 525/314 |
| 5,264,488 A | * | 11/1993 | Takeuchi et al. .............. | 525/89 |
| 6,713,545 B2 | * | 3/2004 | Petiniot et al. ............. | 524/224 |

* cited by examiner

*Primary Examiner*—Jill L. Heitbrink
(74) *Attorney, Agent, or Firm*—Ohlandt, Greeley, Ruggiero & Perle, L.L.P.

(57) ABSTRACT

There is provided a composition comprising a unique polymeric compound that provides a soft, flexible product. There is also provided a unique polymeric tampon applicator that is soft and flexible. When used as a tampon applicator barrel, the barrel is more comfortable and has improved ease of insertion. The polymeric compound primarily comprises a thermoplastic resin and a block copolymer that exhibit unique load, energy and modulus of elasticity properties. The polymeric compound should also include a plasticizer and a compatibilizer/flow modifier, and may include a slip/mold release agent, an antioxidant, and even a pigment. There is also provided a method for making the polymeric compound that will be formed into a product, such as an applicator or applicator barrel in which all of the above ingredients, except for the thermoplastic resin, are combined and formed into soft pellets. The soft resin pellets are then dry blended with pellets of the thermoplastic resin. The mixture of the thermoplastic resin pellets and the soft resin pellets are then melted and injection molded into the desired shape. There is thus provided a method of making a soft, polymeric tampon applicator or tampon applicator barrel.

19 Claims, No Drawings

SOFT, FLEXIBLE COMPOSITION AND METHOD FOR MAKING SAME

RELATED APPLICATIONS

This application is a continuation-in-part of application Ser. No. 09/648,883 filed on Aug. 25, 2000, issued as U.S. Pat. No. 6,756,434, which is a divisional of application Ser. No. 09/075,097 filed May 8, 1998 and issued into U.S. Pat. No. 6,254,565, which is a continuation of application Ser. No. 08/547,766 filed Oct. 24, 1995 and issued as U.S. Pat. No. 5,986,000, which is a continuation-in-part of application Ser. No. 08/447,289 filed May 22, 1995 and issued as U.S. Pat. No. 5,681,894; of which, each of the above-cited applications are incorporated in their entirety by reference herein.

BACKGROUND OF THE INVENTION

I. Field of the Invention

The present invention relates generally to a soft, flexible material. More particularly, it relates to a thermoplastic composition that can be used to make a variety of products that are soft and flexible. The thermoplastic composition is, preferably, a combination of a polyolefin and thermoplastic elastomeric materials. In addition, the thermoplastic composition may include one or more additional thermoplastic materials. Some uses envisioned for this composition are, for example, catamenial devices, baby care products, such as baby bottles and holders, pacifiers, toothbrushes and containers. One particular use of the composition is for a tampon applicator and especially a tampon applicator barrel, that will be more comfortable and has a greater ease of insertion into the vagina greater ease of insertion into the vagina than known such applicator barrels.

II. Description of the Prior Art

Polyethylene is a thermoplastic that is the standard resin used to produce a number of products, including plastic tampon applicators. A softer applicator, especially an applicator barrel that is more comfortable is a desirable feature of a tampon applicator in order to provide improved ease of insertion.

It is generally known that thermoplastic elastomer articles may be combined with polyethylene to improve the strength and toughness of such articles. For example, U.S. Pat. No. 4,593,063 to M. A. Jones, et al., which issued Jun. 3, 1986, provides a reinforced rigid polymer blend, which yields a high gloss finish when injection molded. The thermoplastic elastomer includes 25 to 35 percent of a butadiene thermoplastic elastomer having a molecular weight of about 70,000 to about 100,000, a styrene content from about 25 to about 44 percent by weight and a melt flow rate from about 8 to about 15 grams per 10 minutes. The butadiene thermoplastic elastomer is blended with from about 54 to about 75 percent of a rigid polymer, such as polyethylene.

Polymers have also been combined with polyethylene to improve their reaction to each other when heated or otherwise processed. For example, U.S. Pat. No. 4,678,834 to D. W. Boivin, et al., which issued Jul. 7, 1987, provides a polyolefin blend comprising a major portion of polyethylene and a minor portion of a second polymer, such as a styrene-butadiene-styrene copolymer. The second polymer contains a reactive agent that is capable of reacting with polyolefins in a molten state. The reactive agent modifies or stabilizes the polymer during processing or during use.

Polymers may also be added to polyethylene to permit a breakdown of its structural composition. Polyethylene, which is normally stable, has also been combined with less stable materials to produce biodegradable products. Such biodegradable products include ingredients that cause oxidative actions in order to break down the polyethylene. For example, U.S. Pat. No. 5,212,219 to G. J. L. Griffin, which issued May 18, 1993, provides a degradable article prepared from a blend of polyethylene and a less stable polymer or copolymer, such as a styrene-butadiene block copolymer. The composition further comprises an antioxidant active over a limited period and a pro-oxidant that causes a sharp loss of physical strength on depletion of the anti-oxidant. In addition, the presence of filler particles of a biologically sensitive material accelerates the biological breakdown of the polymer/copolymer blend.

Improvements to the pelletizability and drapability of a polymer composition, without causing the composition to biodegrade, are also known. For example, U.S. Pat. No. 4,833,195 to A. M. Adur, et al., which issued May 23, 1989, provides a thermoplastic polymer composition that can be conveniently converted into a drapable film or fabric. The composition has a low Shore A hardness, i.e., below about 95, and a high melt flow rate about 30 grams/10 minutes to 1100 grams/10 minutes at 230 degrees Celsius and 2.16 kilograms. Drapability is an important property of products that drape against a user's skin, such as baby diapers or sanitary napkins.

However, none of the above patents describe or suggest a tampon applicator that is composed of such materials. In fact, none of the above patents suggest the inventive combination of polyethylene and the unique elastomeric composition which improves flexibility, strength and tear resistance and, perhaps, softness, and can function as a compatibilizer with other thermoplastic polymeric materials. Thus, the above patents do not suggest a flexible, soft tampon applicator having a unique blend of polyethylene and a rubber type composition that includes a thermoplastic elastomer (TPE), namely a styrene-butadiene-styrene block copolymer, which applicator provides for comfortable and easy insertion into the vagina.

Further, thermoplastic resins are much less expensive than elastomeric materials. To minimize the costs of tampon applicators, one desires the greatest amount of thermoplastic resin as possible in the composition, but without adverse affects. Accordingly, to achieve the benefits of a flexible and easy to insert tampon applicator barrel and yet minimize costs, it is desired to use as little as possible of the elastomer components and as much as possible of the thermoplastic resin component in the tampon applicator barrel.

Other projected products, such as, for example, a holder for nurser liners or a nurser bottle, may desire the flexibility of the material in order to assist a child or parent in gripping the product and, perhaps, squeeze the product to remove contents.

SUMMARY OF THE INVENTION

Against the foregoing background, it is a primary object of the present invention to provide a composition that comprises a polyolefin and a thermoplastic elastomer.

It is another object of the present invention to provide such a composition that favorably adjusts the modulus of elasticity of the composition.

It is yet another object of the present invention to provide such a composition in a thermoplastic-type tampon applicator so that the barrel, in particular, is soft and flexible to provide more comfort and improved ease of insertion.

It is a further object of the present invention to provide such a tampon applicator having at least one styrene-butadiene-styrene block copolymer to achieve such desired properties.

To accomplish the foregoing objects and advantages, the present invention, in brief summary, is a soft, flexible composition that comprises a thermoplastic resin and at least two styrene-butadiene-styrene block copolymers, each having a different percent by weight of styrene in an amount sufficient to reduce the modulus of elasticity.

A preferred use of the composition is as a tampon applicator barrel that is more comfortable and has improved ease of insertion into the vagina. The tampon applicator barrel comprises a thermoplastic resin and at least one thermoplastic elastomer in an amount sufficient to adjust favorably the modulus of elasticity of the tampon applicator barrel.

More specifically, the present invention is a soft, flexible tampon applicator that provides more comfort and improved ease of insertion into the vagina by the combination of a low density polyethylene and at least one styrene-butadiene-styrene block copolymer. In one preferred embodiment, there are at least two styrene-butadiene-styrene block copolymers, each having a different percent by weight of styrene.

In a most preferred embodiment, there are three styrene-butadiene-styrene block copolymers each having a percentage by weight of styrene that is different than that of the other two copolymers. In particular, the first styrene-butadiene-styrene block copolymer has about 29 percent by weight of styrene, the second styrene-butadiene-styrene block copolymer has about 31 percent by weight of styrene, and the third styrene-butadiene-styrene block copolymer has about 43 percent by weight of styrene.

The polymeric resin should further comprise one or more of the following: a plasticizer and a compatibilizer/flow modifier, and may further comprise other ingredients, such as a pigment, a slip/mold release agent, an antioxidant and, perhaps, an antistat ingredient.

The present invention is also a method for making a composition that can be made into a soft, flexible product. An elastomer composition is melted and combined to form a melted resin, which is then extruded into a plurality of soft resin pellets. The plurality of soft resin pellets are then dry blended with a plurality of pellets of a polyolefin, for example, low density polyethylene to form a pellet mixture. Finally, the pellet mixture is melted together to form a polymeric compound that may be molded to a desired shape. In a preferred embodiment, the method is used to make a tampon applicator, especially an applicator barrel that has a soft and flexible structure for more comfort and improved ease of insertion into the vagina.

DETAILED DESCRIPTION OF THE PREFERRED EMBODIMENT

The present invention provides a new polymeric compound or composition that is a combination of a polyolefin and a rubber type composition that adjusts the softness and flexibility of the polymeric compound. As stated above, while it is envisioned that this material may be used to form a variety of products, such as, for example, baby or nurser bottles and holders, pacifiers, toothbrushes and containers, a preferred application is for catamenial devices. A particularly preferred application is a tampon applicator, especially an applicator barrel, composed of this new polymeric compound.

To minimize costs, it is preferable that the tampon applicator have an applicator barrel that uses the polymeric compound of the present invention, while the plunger is made, perhaps, of less expensive material. A softer applicator barrel is more comfortable and is a desirable feature of a tampon applicator in order to provide improved ease of insertion. Accordingly, the present application is directed to a tampon applicator barrel, however it can be used for the entire tampon applicator.

The polymeric compound comprises polyolefin and a rubber type composition that adjusts the softness and flexibility of the polymeric compound and, thus, the tampon applicator. For the preferred embodiment, the polyolefin is a low density polyethylene and the rubber type composition includes a thermoplastic elastomer. The thermoplastic elastomers could include thermoplastic vulcanizates, thermoplastic olefins, styrene block copolymers, thermoplastic urethanes and combinations thereof. In the most preferred embodiment, the thermoplastic elastomer is a plurality of styrene-butadiene-styrene block copolymers.

The primary supporting structure of the soft applicator barrel is provided by the polyolefin. The preferred type of polyolefin is polyethylene, and, more preferably, low density polyethylene. The polyethylene can be a linear low density polyethylene. For the preferred embodiment, the polyolefin is about 25 to about 75 percent by weight of the total weight of the polymeric compound.

The thermoplastic elastomers are combined with the polyolefin in amounts sufficient to adjust the elasticity of the polymeric compound.

Styrene-butadiene-styrene block copolymers are the preferred thermoplastic elastomers. A combination of three different types of styrene-butadiene-styrene block copolymers having different contents of styrene is the more preferred. In a most preferred embodiment, a first styrene-butadiene-styrene block copolymer has 29 percent by weight of styrene in the block copolymer, a molecular weight of 80,000 and a melt flow rate 8 grams per 10 minutes, a second styrene-butadiene-styrene block copolymer has 31 percent by weight of styrene, a molecular weight of 100,000 and a melt flow rate less than 1 gram per 10 minutes, and a third styrene-butadiene-styrene block copolymer has 43 percent by weight of styrene, a molecular weight of 58,000 and a melt flow rate 23 grams per 10 minutes. The melt flow rate for all three styrene-butadiene-styrene block copolymers is measured at 200 degrees Celsius with a 5.0 kg load. Such first, second and third styrene-butadiene-styrene block copolymers are commercially available as Vector Resin 8550, Vector Resin 2518, and Vector Resin 6241, respectively. These copolymers are manufactured by Dexco Polymers (a Dow/Exxon Partnership) of Houston, Tex.

Each of the first, second and third styrene-butadiene-styrene block copolymers is about 5.5 to about 16.6 percent by weight of the total weight of the polymeric compound. Accordingly, the weight of the block copolymers is about 16.5 to about 49.80 percent by weight of the total weight of the polymeric compound.

The combination of these three block copolymers has been found to provide the optimum viscosity desired so that the thermoplastic resin phase, namely polyethylene, and the rubber phase are compatible.

The rubber type composition that is added to the polyolefin may also include other materials. It is preferred that a plasticizer, such as mineral oil, be used to reduce the viscosity and hardness. The plasticizer is about 5 to about 15 percent by weight of the total weight of the polymeric compound. In addition, the rubber type composition may contain a filler, such as CaCO3 or talc.

It is also preferred that the polymeric compound include a compatibilizer/flow modifier, which assists in the blending or compatibilization of the thermoplastic resin and the rubber materials, and to improve the tear resistance and elongation properties of the compound. Preferably, the compatibilizer/flow modifier is a copolymer. In the preferred embodiments, the copolymer is an alpha olefin copolymer, namely an ethylene copolymer. In the most preferred embodiment, the ethylene copolymer is ethylene methyl acrylate. Alternative alpha olefin copolymers that can be used are ethylene vinyl acetate, ethylene ethyl acrylate, ethylene butyl acrylate and mixtures thereof. Ethylene methyl acrylate is the most preferred since it, unlike ethylene vinyl acetate, will not decompose under high molding temperatures, and is less expensive than either ethylene ethyl acrylate or ethylene butyl acrylate.

The compatibilizer/flow modifier is present in an amount about 2.9 to about 8.6 percent by weight of the total weight of the polymeric compound.

The rubber type composition may further include additives, such as a pigment or color additive, a slip/mold release agent, an antioxidant and/or an antistat, that may be necessary to facilitate the manufacture or otherwise improve the quality of the tampon applicator or barrel.

The pigment, that is chosen to provide the desired aesthetic effect, is preferably titanium dioxide. It is about 0.5 to about 1.5 percent weight of the total weight of the polymeric resin.

The slip/mold release agent is, preferably, a fatty acid amide, such as, erucamide. Alternatively, the slip/mold release agent can be metallic stearates, calcium stearate, ethylene bis stearamide and ethylene bis oleamide. In a preferred embodiment for use in a tampon applicator barrel, erucamide is present in an amount about 0.8 percent by-weight of the total weight of the polymeric compound. While erucamide is a preferred slip release agent, an erucamide slip agent may undergo substantial blooming subsequent to molding. Such blooming will result in an agglomeration of the erucamide slip release agent on the surface of the molded polymeric article that can cause gumming and contamination problems in equipment if substantial post-molding handling of the article is required. Surprisingly, stearyl erucamide has been found to avoid the blooming problem. The use of higher amounts, about 3%, of stearyl erucamide is preferred. Accordingly, stearyl erucamide has been found to particularly improve the process of manufacture of a tampon applicator and tampon applicator barrel that require significant handling after molding. When stearyl erucamide is used, a higher amount of the release agent, for example up to about 3 percent by weight of the total weight of the composition, may be used. Accordingly, the slip/mold release agent can be present in a range about 0.4 to about 3 percent by weight of the total weight of the polymeric compound.

The antioxidant provides stability to the polymeric compound. It is preferred that the antioxidant be a combination of two antioxidants. One antioxidant is tetrakis [methylene (3,5-di-tert-butyl-4-hydroxyhydrocinnamate)] methane. The other antioxidant is tris (2,4-di-tert-butyl phenyl) phosphite. Such antioxidants/stabilizers are manufactured under the product names Irganox 1010 and Irgafos 168, respectively, by Ciba-Geigy Corporation. Each antioxidant is about 0.05 to about 0.15 percent by weight of the total weight of the polymeric compound.

When there is substantial handling of the molded article, such as, for example, a tampon applicator or tampon applicator barrel, the most preferred embodiment of the present composition has the following ingredients and their approximate percent by weight of the total composition:

TABLE A

| | |
|---|---|
| about 63% | low density polyethylene; |
| about 8% | first styrene-butadiene-styrene block copolymer having about 29 percent of styrene; |
| about 8% | second styrene-butadiene-styrene block copolymer having about 31 percent of styrene; |
| about 8% | third styrene-butadiene-styrene block copolymer having about 43 percent of styrene; |
| about 7% | mineral oil as the plasticizer; |
| about 4% | ethylene methyl acrylate as the compatibilizer/flow modifier; |
| about 1% | titanium dioxide as the pigment; |
| about 1.5% | stearyl erucamide as the slip/mold release agent; |
| less than 1% | tetrakis [methylene(3,5-di-tert-butyl-4-hydroxyhydrocinnamate)] methane as a stabilizer/antioxidant; and |
| less than 1% | tris(2,4-di-tert-butyl phenyl) phosphite as a stabilizer/antioxidant. |

Higher styrene contents would tend to make the elastomer material less soft and less flexible. In a preferred embodiment of the polymeric compound, the amount of the third styrene-butadiene-styrene block copolymer is about one-half of one percent less than the amount of the first or second styrene-butadiene-styrene block copolymers.

It is to be understood that an antistatic agent or antistat may be added to the polymeric compound but is not a part of the preferred embodiment. The antistat imparts a slight to moderate degree of electrical conductivity to plastic compounds, thus preventing the accumulation of electrostatic charges on the soft applicator. The antistat may be incorporated in the ingredients before molding, or applied to the outer surface of the tampon applicator or barrel after molding.

The preferred method for making the preferred polymeric compound that is formed into an applicator or applicator barrel is as follows. The three styrene-butadiene-styrene block copolymers, mineral oil, ethylene methyl acrylate, stearyl erucamide and the antioxidants (and pigment, if used) are weighed and then combined in a twin screw extruder that melts and blends the ingredients and forms a melted resin. The melted resin is then extruded and cut into soft resin pellets. These soft resin pellets are then dry blended with pellets of the remaining ingredient, i.e. the low density polyethylene, to form a pellet mixture. The pellet mixture of low density polyethylene pellets and soft resin pellets are then melted and injection molded to form the desired shape for the soft tampon applicator or applicator barrel.

An alternative method for making the preferred polymeric compound that is formed into an applicator or applicator barrel includes weighing all ingredients including the low density polyethylene and then combining them in a twin screw extruder to form the melted compound. The melted compound is then extruded and cut into pellets which are then injection molded to form the desired shape for the tampon applicator or applicator barrel.

In order to exemplify the effectiveness of the composition comprising low density polyethylene and the styrene-butadiene-styrene block copolymers verses conventional low density polyethylene based compositions, the following comparison test was conducted of tampon applicator barrels.

An element of "softness" is flexibility. In order to test for flexibility, Instron compression testing was performed to compare differences in flexibility of the tampon applicator barrel of the preferred embodiment against the four known thermoplastic applicator barrels.

The Instron compression test was designed to treat the whole barrel as a tubular specimen. A ⅝ inch wide platen is used to radially compress the applicator barrel against a 6 inch anvil. The specimen is placed on the anvil so that the platen engages the barrel at an axial location between 13/8 inch and 23/16 inch as measured from the finger grip end of the applicator barrel. The specimen is compressed by a total of 0.25 inch at a rate of 0.5 inch/minute.

As shown in Table B below, the Instron compression test produced the following results.

TABLE B

Instron Compression Testing

| | LOAD lbs. (std. dev.) | YOUNG'S MODULUS PSI (std. dev.) | ENERGY lbs.-inch (std. dev.) |
|---|---|---|---|
| Tampon applicator barrels having an outside diameter about 0.67 inches +/− .07 inches and a wall thickness about .027 inches +/− .003 inches | | | |
| Known Branded Thermoplastic applicators | 2.22 to 3.59 (0.16) (0.22) | 191.9 to 277.5 (20.4) (28.9) | 0.28 to 0.46 (0.02) (0.03) |
| Preferred Composition Applicator | 1.74 (0.10) | 104.2 (11.8) | 0.22 (0.01) |
| Tampon applicator barrels having an outside diameter about 0.56 inches +/− .06 inches and a wall thickness about .027 inches +/− .003 inches | | | |
| Known Branded Thermoplastic applicators | 3.11 to 4.85 (0.28) (0.27) | 239.4 to 474.8 (26.6) (59.3) | 0.40 to 0.62 (0.04) (0.05) |
| Preferred Composition Applicator | 1.96 (0.20) | 113.0 (17.6) | 0.25 (0.03) |

The standard deviation of the four known branded thermoplastic applicator barrels is different for each applicator barrel. Accordingly, there is a range for the known thermoplastic applicators with a standard deviation for the lowest number and largest number in the range. It should be understood that the grade of material, diameter and wall thickness of the barrel are the three factors that affect flexibility, and that flexibility is determined by the load, Young's modulus or modulus of elasticity, and energy.

Young's modulus, also known in the art as modulus of elasticity, is a measurement for flexibility. It is the ratio of a nominal stress to corresponding strain below the proportional limit of a material. Young's modulus is expressed in force per unit area, usually lbs. per square inch (PSI) as shown in Table B.

The larger diameter, preferred composition applicator has an outside diameter about 0.60 inches. As shown in Table B, it has been found significantly more flexible than known thermoplastic applicators. For the larger outside diameter applicator barrels, about 0.60 to about 0.74 inches (0.67 inches+/−0.07 inches), the load results indicate that the applicator barrel made with the preferred polymeric compound requires about 1.74 lbs. to radially compress the applicator barrel by 0.25 inches, whereas the known thermoplastic applicator barrels require about 2.22 lbs. to about 3.59 lbs. In addition, Young's modulus or the modulus of elasticity for the present applicator barrel is about 104 psi, whereas the known thermoplastic applicators is about 192 psi to about 278 psi. Also, the energy to compress by 0.25 inches the present applicator barrel is about 0.22 lbs.-inch, whereas the known applicator barrels are about 0.28 to 0.46 lbs.-inch. Preferably, with barrels of this dimension, the thermoplastic elastomer will be used in an amount sufficient to adjust the energy needed to compress the tampon applicator barrel by 0.25 inches to less than 0.26 lbs.-inch and adjust the supportable load of the tampon applicator to less than about 2.06 lbs.

It would be expected that the smaller the outside diameter of the barrel, the higher the Young's modulus. Accordingly, the results of the present applicator barrel (having an outside diameter of about 0.60 inches) to the known applicator barrels having an outside diameter from 0.60 to 0.74 is even more remarkable.

For the smaller outside diameter applicator barrels, i.e. about 0.50 to about 0.62 inches (0.56 inches+/−0.06), the load results indicate that the applicator barrel made with the preferred polymeric compound (having an outside diameter about 0.54 inches) requires about 1.96 lbs. to radially compress the applicator barrel 0.25 inches, whereas the known thermoplastic applicator barrels require about 3.11 lbs. to about 4.85 lbs. to compress 0.25 inches. In addition, the modulus of elasticity for the present applicator barrel is about 113 psi, whereas the modulus of elasticity for the known thermoplastic applicator barrels is about 240 psi to about 475 psi. Also, the energy to compress by 0.25 inches the present applicator barrel is about 0.25 lbs.-inch, whereas such energy to compress the known applicator barrels the same amount is about 0.40 to 0.62 lbs.-inch. Preferably, with barrels of this dimension, the modulus of elasticity will be less than 79 psi, and the thermoplastic elastomer will be used in an amount sufficient to adjust the energy needed to compress the tampon applicator barrel by 0.25 inches to less than 0.36 lbs.-inch and adjust the supportable load of the tampon applicator to less than about 2.83 lbs.

Thus, present or soft applicators made with the preferred polymeric compound of the present invention have a load, modulus of elasticity and energy approximately one-half that of all known thermoplastic applicator barrels. In addition, applicator barrels of the present invention have been found by consumers as a unique, softer applicator barrel due to the tactile feel of the applicator barrels.

In addition to improved "softness" and "flexibility", the polymeric compound or composition of the present composition has been found to have improved strength and tear resistance. The following test demonstrates the unexpected improvement in strength and tear resistance.

Samples A through D were manufactured by combining three block copolymers, a plasticizer, a compatibilizer/flow modifier, mold release agents, antioxidants/stabilizers and a pigment, and in the percentages set forth in Table C. They were compared with a "comparative" sample made of a combination of one block copolymer, along with an analogous plasticizer, mold release agents, antioxidants/stabilizers and pigment. For each sample and the comparative, the mixed compositions were made according to the preferred method set forth above. In particular, each mixed composition was passed through a twin screw extruder that melted and blended the ingredients and extruded to form a melted resin that is then cut into soft resin pellets. The soft resin pellets were then dry blended with pellets of low density polyethylene to form a pellet mixture. The pellet mixture was then melted and injection molded to form ASTM test articles. The four samples and the comparator were evaluated for elongation, tensile strength, and tear resistance (see Table D). As evidenced by the results of Table D, the four samples, each with three block copolymers, as compared to the one block copolymer comparative, demonstrated significantly improved strength and tear resistance properties.

In addition, the preferred composition noted as D in Table D and also set forth in Table A, has the best combination of softness, flexibility, strength and tear resistance of all compositions tested.

TABLE C

| Ingredients | A | B | C | D | Comparative |
|---|---|---|---|---|---|
| Styrene-butadiene-styrene (29% styrene) | 10.48 | 8.90 | 11.93 | 8.0 | 29.97 |
| Styrene-butadiene-styrene (31% styrene) | 10.48 | 8.90 | 11.93 | 8.0 | — |
| Styrene-butadiene-styrene (43% styrene) | 7.20 | 8.32 | 8.22 | 8.0 | — |
| Mineral Oil | 7.13 | 8.12 | 8.12 | 7.0 | 10.23 |
| Ethylene-methyl acrylate (20MI) | — | 4.68 | — | 4.0 | — |
| Stearyl erucamide | — | 1.83 | — | 1.5 | 0.63 |
| Irganox 1010 | <0.1 | <0.1 | <0.1 | <0.1 | <0.1 |
| Irgafos 168 | — | <0.1 | <0.1 | <0.1 | <0.1 |
| Low density polyethylene | 58.40 | 58.40 | 58.20 | 63.0 | 58.20 |
| Ethylene vinyl acetate | 4.80 | — | — | — | — |
| Titanium | 0.80 | 0.78 | 0.80 | 1.0 | 0.80 |
| Erucamide | 0.64 | — | 0.63 | — | 0.63 |

TABLE D

| | Sample | | | | |
|---|---|---|---|---|---|
| | A | B | C | D | Comparative |
| Elongation, % (ASTM D638) | 170 | 246 | 162 | 227 | 86 |
| Tensile Strength psi (ASTM D638) | 820 | 878 | 862 | 917 | 753 |
| Tear Resistance (ASTM D624) | 218 | 234 | 167 | 248 | 132 |

The present invention having been thus described with particular reference to the preferred forms thereof, it will be obvious that various changes and modifications may be made therein without departing from the spirit and scope of the invention as defined in the appended claims.

We claim:

1. A method for making a tampon applicator barrel having a soft, flexible supporting structure comprising the steps of:
   providing an elastomeric composition with at least two styrene-butadiene-styrene block copolymers;
   melting said elastomeric composition thereby forming a melted resin;
   extruding said melted resin into a plurality of soft pellets;
   dry blending said plurality of soft pellets with a plurality of pellets comprising low density polyethylene to form a pellet mixture;
   melting said pellet mixture to form a polymeric compound; and
   molding said polymeric compound to a desired shape to form the tampon applicator barrel.

2. The method of claim 1, wherein said at least two styrene-butadiene-styrene block copolymers is at least three styrene-butadiene-styrene block copolymers.

3. The method of claim 1, wherein said at least two styrene-butadiene-styrene block copolymers each have a different percentage by weight of styrene present in amounts sufficient to adjust an elasticity of said composition.

4. The method of claim 2, wherein said at least three styrene-butadiene-styrene block copolymers each have a different percentage by weight of styrene present in amounts sufficient to adjust an elasticity of said composition.

5. The method of claim 1, wherein said elastomeric composition further comprises one or more compounds selected from the group consisting of plasticizer, compatibilizer/flow modifier, slip/mold release agent, antioxidant, and any combinations thereof.

6. The method of claim 2, wherein at least one of said at least three styrene-butadiene-styrene block copolymers has about 29 wt. % styrene.

7. The method of claim 2, wherein at least one of said at least three styrene-butadiene-styrene block copolymers has about 31 wt. % styrene.

8. The method of claim 2, wherein at least one of said at least three styrene-butadiene-styrene block copolymers has about 43 wt. % styrene.

9. The method of claim 2, wherein said at least three styrene-butadiene-styrene block copolymers has a first styrene-butadiene-styrene block copolymer with about 29 wt. % styrene, a second styrene-butadiene-styrene block copolymer with about 31 wt. % styrene, and a third styrene-butadiene-styrene block copolymer with about 43 wt. % styrene.

10. The method of claim 1, wherein said at least two styrene-butadiene-styrene block copolymers are present in an amount about 16.5 wt. % to about 49.8 wt. %, based on the total weight of the composition.

11. The method of claim 1, wherein said low density polyethylene is present in an amount about 25 wt. % to about 75 wt. %, based on the total weight of the composition.

12. The method of claim 5, wherein said compatibilizer/flow modifier is an ethylene copolymer.

13. The method of claim 5, wherein said compatibilizer/flow modifier is ethylene methyl acrylate.

14. The method of claim 5, wherein said compatibilizer/flow modifier is present in an amount about 2.9 wt. % to about 8.6 wt. %, based on the total weight of the composition.

15. The method of claim 5, wherein said plasticizer is mineral oil.

16. The method of claim 5, wherein said plasticizer is present in an amount about 5 wt. % to about 15 wt. %, based on the total weight of the composition.

17. The method of claim 5, wherein said slip/mold release agent is stearyl erucamide.

18. The method of claim 5, wherein said antioxidant is selected from the group consisting of tetrakis [methylene(3,5-di-tert-butyl-4-hydroxyhydrocinnamate)] methane, tris(2,4-di-tert-butyl phenyl) phosphite, and any combinations thereof.

19. The method of claim 5, wherein said antioxidant is present in an amount about 0.05 wt. % to about 0.15 wt. %, based on the total weight of the composition.

* * * * *